United States Patent [19]

Bowie et al.

[11] Patent Number: 4,672,036

[45] Date of Patent: Jun. 9, 1987

[54] **PURE CULTURES OF *KIBDELSPORANGIUM ARIDUM* SHEARER GEN. NOV., SP. NOV. ATCC 39323 AND MUTANTS THEREOF**

[75] Inventors: Betty A. Bowie, Havertown; David J. Newman, Wayne; Marcia C. Shearer, Conshohocken, all of Pa.

[73] Assignee: SmithKline Beckman Corporation, Philadelphia, Pa.

[21] Appl. No.: 749,029

[22] Filed: Jun. 26, 1985

Related U.S. Application Data

[62] Division of Ser. No. 513,513, Jul. 13, 1983, Pat. No. 4,548,974.

[51] Int. Cl.$^4$ .................... C12N 1/14; C12R 1/645
[52] U.S. Cl. .................... 435/254; 435/911
[58] Field of Search ............ 424/118; 435/169, 911, 435/254

[56] References Cited

U.S. PATENT DOCUMENTS

| | | | |
|---|---|---|---|
| 4,122,168 | 10/1978 | Michel | 424/118 |
| 4,322,406 | 3/1982 | Debono et al. | 424/118 |
| 4,378,348 | 3/1983 | Nishida et al. | 424/118 |

OTHER PUBLICATIONS

Williams et al., "Topics in Antibiotic Chemistry", vol. 5, pp. 119–158.

*Primary Examiner*—Thomas G. Wiseman
*Assistant Examiner*—Elizabeth C. Weimar
*Attorney, Agent, or Firm*—Edward T. Lentz; Janice E. Williams; Alan D. Lourie

[57] ABSTRACT

A novel antibiotic complex of "vancomycin-like" antibiotics, AAD 216 complex, is produced by the cultivation of a fermentation broth containing *Kibdelosporangium aridum* Shearer gen. nov., sp. nov. ATCC 39323 microorganisms in an aqueous nutrient medium under submerged aerobic conditions. The AAD 216 complex and its major bioactive components; AAD 216A, AAD 216B, and AAD 216C exhibit antibiotic activity and growth promotant activity.

2 Claims, No Drawings

PURE CULTURES OF *KIBDELSPORANGIUM ARIDUM* SHEARER GEN. NOV., SP. NOV. ATCC 39323 AND MUTANTS THEREOF

This is a division of application Ser. No. 513,513 filed July 13, 1983 now U.S. Pat. No. 4,548,974.

SUMMARY OF THE INVENTION

This invention relates to new antibiotics of the vancomycin-class and the production and recovery thereof. This invention also relates to the new microorganism *Kibdelosporangium aridum* Shearer, gen. nov., sp. nov. SK&F-AAD 216 (ATCC 39323). More particularly, this invention relates to an antibiotic, designated herein AAD 216 complex, said complex being produced by cultivating *K. aridum* in an aqueous nutrient medium, containing assimilable sources of nitrogen and carbon, under submerged aerobic conditions until a substantial amount of AAD 216 complex is produced by said microorganism in said medium and optionally recovering AAD 216 complex from the culture medium.

Also provided for in this invention are the novel bioactive components of the AAD 216 complex; AAD 216A, AAD 216B and AAD 216C, which are prepared by the separation and isolation of the individual antibiotic compounds from the AAD 216 complex by chromatographic means. The antibiotic, AAD 216 complex and its major bioactive components; AAD 216A, AAD 216B and AAD 216C all exhibit antibacterial activity. The AAD 216 complex, AAD 216A, AAD 216B and AAD 216C are also useful in animal health applications, such as a growth promotant and the treatment of bovine mastitis.

DETAILED DESCRIPTION

The new antibiotics, AAD 216 complex and its major bioactive components; AAD 216A, AAD 216B and AAD 216C, are produced by the fermentation of a new microorganism *Kibdelosporangium aridum* Shearer gen. nov., sp. nov. SK&F-AAD 216. The above microorganism was isolated from a soil sample collected in a desert area near Pima, Ariz. A culture of the biologically pure microorganism has been deposited in the American Type Culture Collection, Rockville, Md. as the type culture under accession number ATCC 39323.

The AAD 216 complex refers to the mixture of the individual antibiotics produced by the fermentation of *K. aridum*. As is readily understood by those familiar with antibiotics fermentation processes, the ratios of the individual or factor antibiotics and their presence in the AAD 216 complex will vary, depending on the conditions of the fermentation process. The AAD 216 complex may be recovered from the fermentation medium by clarifying the whole fermentation broth by filtration and by precipitating the crude AAD 216 complex at 0° to 10° C. with hydrochloric acid at a pH of 3. The precipitate is then dissolved in water by adjusting the pH to about 6 to 8 and applied to a resin column from which it is eluted with aqueous methanol. The resultant eluant is lyophilized to yield the AAD 216 complex which is chromatographed to afford the enriched AAD 216 complex. Typically, the enriched AAD 216 complex contains 40 to 85 percent by weight of a mixture of AAD 216A, AAD 216B and AAD 216C.

The enriched AAD 216 complex at a pH of about 6 which by analytical HPLC contains by weight 29 percent AAD 216A, 10 percent AAD 216B and 10 percent AAD 216C has the following characteristics:

(a) pale-white-yellow solid which decomposes at 300° to 350° C.;

(b) an approximate elemental composition of 53.22 percent carbon, 6.14 percent hydrogen, 3.73 percent nitrogen and 0.28 percent ash;

(c) an infrared spectrum in potassium bromide which exhibits peaks at the following wave numbers in $cm^{-1}$: 3400, 2920, 1660, 1600, 1510, 1460, 1430, 1390, 1320, 1240, 1150, 1060 and 1020;

(d) an ultraviolet spectrum in acetonitrile:water (1:1) which exhibits an absorption maximum at 280 nm under neutral and acid conditions with an $E_{1\%}=43.9$ and at 301 nm under basic conditions with an $E_{1\%}=56.8$;

(e) a positive reaction with periodate and negative reaction with ninhydrin; and (f) soluble in $H_2O$, methanol, dimethylsulfoxide and dimethylformamide and insoluble in ethanol, acetonitrile, acetone, diethylether and aliphatic hydrocarbons.

The individual pure antibiotic components, AAD 216A, AAD 216B and AAD 216C can be isolated from the AAD 216 complex utilizing preparative high pressure liquid chromatography (HPLC). Typically, the AAD 216 complex is chromatographed with a step gradient elution with 20 to 28 percent acetonitrile in 0.1N phosphate buffer at pH 6. The appropriate fractions, as determined by analytical HPLC, are combined and desalted on a resin column and after lyophilization affords the desired individual antibiotic components, as pure AAD 216A, AAD 216B and AAD 216C.

AAD 216A antibiotic at a pH of about 6 has the following characteristics:

(a) pale white-yellow solid which decomposes at 300° to 350° C.;

(b) an empirical formula $C_{81}H_{82}N_8O_{30}Cl_4$ (c) an approximate elemental composition of 48.20 percent carbon, 5.01 percent hydrogen, 5.21 percent nitrogen, 6.43 percent chlorine, no sulfur or organic phosphorus, when the water content was 10.80 percent;

(d) an infrared absorption spectrum in potassium bromide which exhibits peaks at the following wave numbers in $cm^{-1}$: 3400, 2920, 1660, 1600, 1510, 1460, 1430, 1390, 1320, 1300, 1240, 1150, 1060 and 1020;

(e) a fast atom bombardment (FAB) mass spectrum with M+H at 1787 (major cluster);

(f) an ultraviolet spectrum in acetonitrile: water (1:1) which exhibits an absorption maximum at 280 nm under neutral and acidic conditions with an $E_{1\%}=51$ and at 301 nm under basic conditions with an $E_{1\%}=73$;

(g) a carbon magnetic resonance spectrum at 90.56 MHz in $CD_3OD:D_2O$ (1:9) at a pH of 8.5 which exhibits the following chemical shifts in part per million (ppm) relative to TMS as standard: 177.7, 177.5, 175.5, 174.6, 171.5, 170.8, 170.4, 170.2, 169.1, 161.8, 158.6, 157.9, 155.1, 155.0, 152.5, 151.9, 151.6, 150.7, 146.0, 144.3, 141.7, 138.8, 138.3, 136.0, 134.6, 134.5, 133.7, 130.8, 129.8, 129.4, 128.9, 128.6, 127.4, 127.0, 126.2, 125.6, 125.1, 122.7, 122.3, 120.9, 119.6, 118.3, 116.4, 110.5, 109.6, 108.3, 104.2, 103.3, 103.1, 100.7, 98.1, 78.4, 74.4, 73.9, 73.3, 72.0, 71.6, 71.3, 70.7, 67.3, 65.6, 63.6, 62.3, 61.6, 60.2, 56.8, 56.3, 55.8, 54.9, 37.2, 32.7, 32.2, 29.8, 29.6, 29.5, 26.2, 23.0 and 14.5;

(h) a specific rotation $[\alpha]_D^{25}=-66°$ (C=0.3 in $H_2O$);

(i) positive reaction with periodate and negative reaction with ninhydrin;

(j) soluble in H$_2$O, methanol, dimethylsulfoxide, dimethylformamide and insoluble in ethanol, acetonitrile, acetone, diethylether and aliphatic hydrocarbons; and.

(k) pK$_a$ values in acetonitrile:water (3:7) as follows: 3.0, 4.9, 7.4, 8.4, 10.0 and 10.3 pK$_a$ values above 10.3 not determined.

AAD 216B antibiotic at a pH of about 6 has the following characteristics:

(a) pale white-yellow solid which decomposes at 300° to 350° C., (b) an empirical formula C$_{82}$H$_{84}$N$_8$O$_{30}$Cl$_4$ (c) an approximate elemental composition of 49.67 percent carbon, 5.07 percent hydrogen, 5.19 percent nitrogen, 6.70 percent chlorine, no sulfur or organic phosphorus, when the water content is 10.8 percent;

(d) an infrared absorption spectrum in potassium bromide which exhibits peaks at the following wave numbers in cm$^{-1}$: 3400, 2920, 1660, 1600, 1510, 1460, 1430, 1390, 1300, 1240, 1150, 1060 and 1020;

(e) a fast atom bombardment (FAB) mass spectrum with M+H at 1801 (major cluster);

(f) an ultraviolet spectrum in acetonitrile: water (1:1) which exhibits an absorption maximum at 280 nm under neutral and acidic conditions with an E$_{1\%}$=55 and at 301 nm under basic conditions with an E$_{1\%}$=72.5;

(g) a carbon magnetic resonance spectrum at 90.56 MHz in CD$_3$OD:D$_2$O (1:9) at a pH of 8.5 which exhibits the following chemical shifts in parts per million (ppm) relative to TMS as standard: 177.9, 177.4, 175.6, 174.4, 171.6, 170.9, 170.5, 170.4, 169.3, 162.4, 158.7, 158.1, 155.2, 155.0, 152.6, 151.3, 150.7, 146.0, 144.3, 141.3, 138.8, 138.3, 136.1, 134.7, 133.6, 130.7, 129.9, 129.8, 129.4, 129.0, 128.7, 127.7, 127.5, 127.0, 126.3, 125.7, 124.7, 122.8, 122.3, 120.9, 119.9, 119.6, 118.4, 116.7, 110.5, 109.6, 108.5, 104.2, 103.3, 103.1, 100.6, 98.1, 78.5, 74.4, 73.9, 73.4, 72.1, 71.7, 71.2, 70.8, 67.3, 65.5, 63.7, 62.3, 61.6, 60.3, 56.8, 56.2, 55.9, 55.0, 39.6, 37.3, 32.7, 30.2, 30.0, 29.7, 28.4, 27.8, 26.3 and 23.3;

(h) a specific rotation [α]$_D^{25}$= −59° (C=1.0 in H$_2$O);

(i) positive reaction with periodate and negative reaction with ninhydrin;

(j) soluble in H$_2$O, methanol, dimethylsulfoxide, dimethylformamide and insoluble in ethanol, acetonitrile, acetone, diethylether, and aliphatic hydrocarbons; and (k) pK$_a$ values in acetonitrile:water (3:7) as follows: 3.0, 4.5, 7.5, 8.5 and 9.7 pK$_a$ values above 9.7 not determined.

AAD 216C antibiotic at a pH of about 6 has the following characteristics:

(a) pale white-yellow solid which decomposes at 300° to 350° C.;

(b) an empirical formula C$_{83}$H$_{86}$N$_8$O$_{30}$Cl$_4$ (c) an approximate elemental composition of 47.89 percent carbon, 5.09 percent hydrogen, 4.95 percent nitrogen, 6.39 percent chlorine, 3.69 ash, no sulfur or organic phosphorus, when the water content was 8.2 percent;

(d) an infrared absorption spectrum in potassium bromide which exhibits peaks at the following wave numbers in cm$^{-1}$: 3400, 2920, 1660, 1600, 1505, 1430, 1390, 1295, 1240, 1150, 1060 and 1020;

(e) a fast atom bombardment (FAB) mass spectrum with M+H at 1815 (major cluster);

(f) an ultraviolet spectrum in acetonitrile:water (1:1) which exhibits an absorption maximum at 280 nm under neutral and acid conditions with an E$_{1\%}$=51 and at 301 nm under basic conditions with an E$_{1\%}$=75;

(g) a carbon magnetic resonance spectrum at 90.56 MHz in CD$_3$OD:D$_2$O (1:9) at a pH of 8.5 which exhibits the following chemical shifts in parts per million (ppm) using TMS as the internal standard: 177.9, 177.2, 175.7, 173.6, 171.5, 170.8, 170.6, 170.2, 169.3, 158.6, 157.8, 155.2, 154.9, 152.7, 151.9, 150.9, 146.0, 144.3, 141.3, 138.8, 138.4, 136.0, 134.9, 134.7, 133.8, 130.8, 129.9, 129.8, 129.3, 129.1, 127.7, 127.5, 127.0, 126.4, 125.3, 122.7, 121.0, 119.7, 118.3, 116.1, 110.4, 109.6, 108.1, 104.1, 103.2, 101.5, 98.0, 78.6, 74.6, 73.9, 73.4, 72.1, 71.7, 71.3, 70.3, 67.3, 65.1, 63.7, 62.5, 61.6, 60.3, 56.8, 56.3, 55.3, 54.9, 39.7, 37.4, 32.6, 32.3, 30.5, 30.4, 30.2, 29.9, 28.6, 28.1, 26.4, 23.4 and 22.0;

(h) a specific rotation [α]$_D^{25}$= −50.6 (C=0.6 in H$_2$O);

(i) positive reaction with periodate and negative reaction with ninhydrin;

(j) soluble in H$_2$O, methanol, dimethylsulfoxide, dimethylformamide and insoluble in ethanol, acetonitrile, acetone, diethylether and aliphatic hydrocarbons; and (k) pK$_a$ values in acetonitrile:water (3:7) as follows: 3.0, 4.2, 7.2, 8.2, 9.9 and 10.3 pK$_a$ values above 10.3 not determined.

The novelty of AAD 216 complex, and its major bioactive components, AAD 216A, AAD 216B and AAD 216C, was confirmed by comparison with known members of the vancomycin/ristocetin class of antibiotics. Specifically, the Rf values from thin layer chromatography against *B. subtilis* for AAD 216A, AAD 216B and AAD 216C were compared to known antibiotics as shown below in TABLE I.

TABLE I

|  | TLC (Avicel)[1] | | |
| --- | --- | --- | --- |
|  | A | B | C |
| A-35512B | 0.14 | 0.25 | 0, 0.15 |
| A-477 | 0.51 | 0.30, 0.40 | 0, 0.20 |
|  |  |  | 0.67, 0.78 |
| Actaplanin | 0.16 | 0.06 | 0.11 |
| Actinoidins A and B | 0.04, 0.24 | 0.18, 0.43 | 0.05 |
| Avoparcin | 0.15 | 0.13 | 0.07 |
| LL-AM-374 | 0.08 | 0.17 | 0.05 |
| Ristocetin | 0.1 | 0, 0.10 | 0.04 |
| Teichomycin A-2 | 0.34 | 0.12, 0.33, 0.47 | 0.77 |
| Vancomycin | 0.17 | 0, 0.35 | 0.1, 0.6 |
| AAD 216A | 0.35 | 0.33 | 0.83 |
| AAD 216B | 0.38 | 0.35 | 0.83 |
| AAD 216C | 0.44 | 0.34 | 0.82 |

[1] Rf values; detection: *B. subtilis* activity. Underlined value is major active component
A nBuOH:HOAc:H$_2$O (4:1:5)
B nPrOH:Petroleum Ether:conc. NH$_4$OH (4:1:2)
C nPrOH:H$_2$O (6:4)

Additionally, the retention times of AAD 216A, AAD 216B and AAD 216C in reverse phase high pressure liquid chromatography were compared to and found to differ from those of the known antibiotics as shown below in TABLE II.

TABLE II

|  | Retention Time, Min. | |
| --- | --- | --- |
| Antibiotics | System A[a] | System B[b] |
| AAD 216A | 15.3 | 14.5 |
| AAD 216B | 15.9 | 15.2 |
| AAD 216C | 17.2 | 16.1 |
| A 35512B | 5.2* | 6.1* |
| A 477 | 11.7* | 8.9* |
| Actaplanin | 6.3* | 7.5* |
| Actinoidin A/B | 5.5* | 8.1* |
| Avoparcin | 5.8* | 7.6* |

TABLE II-continued

| | | |
|---|---|---|
| LL-AM-374 | 5.1* | 6.8* |
| Ristocetin | 3.6 | 5.4 |
| Teichomycin A-2 | 13.6* | 13.8* |
| Vancomycin | 6.0 | 7.4 |

*major component in multicomponent mixture

| (a)HPLC System A: | column: | Ultrasphere ODS, 5 micron, 4.6 × 150 mm |
|---|---|---|
| | solvent: | 7-34% acetonitrile (7% for 1 minute, then ramp to 34% over 13 minutes and hold at 34%) in pH 3.2, 0.1 M phosphate. |
| | flow: | 1.5 ml/min |
| | detection: | uv 220 nm |
| (b)HPLC System B: | column: | Ultrasphere ODS, 5 micron, 4.6 × 150 mm |
| | solvent: | 5-35% acetonitrile (5% for 1 minute, then ramp to 35% over 13 minutes and hold at 35%) in pH 6.0, 0.025 M phosphate |
| | flow: | 1.5 ml/min. |
| | detection: | uv 220 nm |

Total hydrolysis of AAD 216A, AAD 216B and AAD 216C, individually, in 6N hydrochloric acid at reflux for 18 hours yielded no common amino acids which could be detected in a standard amino acid analysis. The presence of actinoidinic acid, which is common in the vancomycin class of antibiotics, was confirmed in the hydrolysis products by high pressure liquid chromatography and FAB mass spectrum when compared to an authentic sample. Further, hydrolysis of AAD 216A, AAD 216B and AAD 216C, individually, in 1N hydrochloric acid at reflux for 4 hours yielded mannose but not ristosamine, glucosamine or vancosamine.

Bioactive hydrolysis products of the compounds of this invention, including the aglycone of the following structural formula (I)

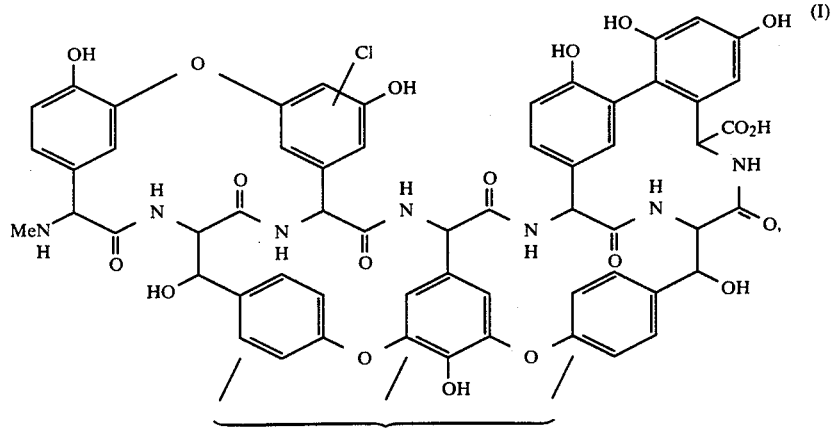

are disclosed and claimed in co-pending U.S. patent application, Attorney Docket No. SKB 14174, filed concurrently herewith.

THE MICROORGANISM

Stock cultures of *Kibdelosporangium aridum* SK&F-AAD 216 (ATCC 39323) were maintained on thin potato-carrot or oatmeal agar. Morphological observations were made on plates of water agar, thin potato-carrot agar, oatmeal agar and soil extract agar. Inoculum for the biochemical and physiological tests was prepared by adding the contents of a frozen vial of vegetative culture to a flask of glucose-yeast extract broth which was placed on a rotary shaker at 28° C., 250 RPM for three to six days. The culture was harvested by centrifugation and washed three times with sterile distilled water. Incubation temperature for the biochemical and physiological tests was 28° C. Readings of the results were made at various times up to 21 days for the plate media. Most of the tubed media were read at various times up to 28 days. However, the tests for decomposition of urea, allantoin and hippurate, as well as the tests for reduction of nitrates, were read for six weeks.

Susceptibility of *K. aridum* to antibiotics was examined by placing BBL susceptibility disks on nutrient agar plates seeded with *K. aridum* as an overlay. Diameters of the zones of inhibition were measured after incubation for one week at 28° C.

MORPHOLOGY

*K. aridum* is a filamentous organism that forms a mycelium differentiated into: (1) a substrate mycelium that penetrates the agar and forms a compact layer on top of the agar, and (2) an aerial mycelium that bears chains of conidia and/or sporangium-like structures. No motile elements were observed in the aerial or substrate mycelium. On many media, *K. aridum* produces characteristic crystals in the agar.

Substrate Mycelium. *K. aridum* produces a well developed, non-fragmenting substrate mycelium. The long branching hyphae are septate and about 0.4 μm–1.0 μm in diameter. Present on the substrate mycelium are specialized structures which consist of dichotomously branched, septate hyphae radiating from a common stalk.

Aerial Mycelium. The aerial mycelium of *K. aridum*, produces chains of rod-shaped, smooth walled spores which are irregular in length (0.4 μm × 0.8 μm–2.8 μm). These spore chains are usually very long with more than 50 spores per chain, but a few short chains of ten spores or less are also usually present. The spore chains may be born apically or on short lateral branches.

On most media, the aerial mycelium of *K. aridum* also produces sporangium-like structures. These may be born apically or on short lateral branches. Sporangium-like structures and chains of spores may be born on the same aerial hyphae. At maturity these sporangium-like structures are round, approximately 9 μm–22 μm in diameter, and consist of septate, branched hyphae embedded in an amorphous matrix which is surrounded by a well-defined wall. When placed on agar, these sporangium-like structures germinate directly with the production of one or more germ tubes.

CHEMOTAXONOMY

Purified cell wall preparations of *K. aridum* analyzed by the method of Becker [Becker et al. Appl. Microbiol. 12, 421-23 (1964)] contained the meso-isomer of 2,6-diaminopimelic acid, alanine, glutamic acid, glucosamine and muramic acid as well as galactose and a very minor amount of arabinose. Whole-cell hydrolysates analyzed by the method of Lechevalier [Lechevalier, M. P., J. Lab. Clin. Med. 71, 934-44 (1968)] contained galactose, glucose, mannose, ribose, rhamnose and arabinose; traces of madurose may also be present. No mycolic acids of any type were present in the cell extracts analyzed for lipid patterns by the method of Lechevalier [Lechevalier et al., Can. J. Microbiol. 19, 965-72 (1973)]. The phospholipids present were phosphatidyl ethanolamine, phosphatidyl methylethanolamine, diphosphatidyl glycerol, phosphatidyl inositol and phosphatidyl inositol mannosides. Thus *K. aridum* has a Type IV cell wall with a whole-cell sugar pattern of Type A with traces of madurose [Lechevalier et al., Int. J. Syst. Bacteriol. 20, 435-43 (1970)] and a phospholipid pattern of type PII with phosphatidyl methylethanolamine [Lechevalier et al., Biochem. System. Ecol. 5, 249-60 (1977)].

PHYSIOLOGICAL AND BIOCHEMICAL CHARACTERISTICS

*K. aridum* is gram positive and not acid-fast. No growth takes place under anaerobic conditions. Temperature range for growth is 15° C. to 42° C. with a trace of growth at 45° C.; no growth occurs at 10° C. or 50° C. Hydrogen sulfide is produced. Milk is peptonized. Gelatin is both hydrolyzed and liquified. Nitrate is not reduced to nitrite. Melanin pigments are produced. Casein, L-tyrosine, hypoxanthine, guanine, elastin and testosterone are hydrolyzed but adenine, xanthine and cellulose (Avicel) are not. Catalase and phosphatase are produced. Urea, esculin and hippurate are decomposed; tests for allantoin decomposition are weakly positive. There is no growth in 8% NaCl; growth in 5% to 7% NaCl is inconsistent. No growth occurs in lysozyme broth. Acid is produced from L-arabinose, D-cellobiose, dextrin, dextrose, D-fructose, glycerol, glycogen, D-galactose, i-inositol, lactose, D-mannitol, D-mannose, α-methyl-D-glucoside, α-methyl-D-mannoside, melibiose, D-melezitose, raffinose, rhamnose, D-ribose, sucrose, trehalose, D-xylose and maltose. No acid is produced from dulcitol, i-erythritol, inulin, D-sorbitol, or L-sorbose. Citrate, malate, succinate, oxalate, lactate, acetate, pyruvate, propionate and formate are utilized; benzoate and tartrate are not.

SUSCEPTIBILITY TO ANTIBIOTICS

By the diffusion method, *K. aridum* was resistant to disks impregnated with gentamicin (10 μg), tobramycin (10 μg), streptomycin (10 μg), vancomycin (30 μg), penicillin (10 units), bacitracin (2 units), lincomycin (2 μg), clindamycin (2 μg), and cephalothin (30 μg). Chlortetracycline (5 g) produced 18 mm zones of inhibition; tetracycline (5 μg) 11-12 mm zones; rifampin (5 μg) 11-15 mm zones; novobiocin (5 μg) 27-28 mm zones. All zones of inhibition contained at least a few resistant colonies.

DESCRIPTION OF *K. ARIDUM* ON VARIOUS MEDIA

All cultures were incubated at 28° C. in closed petri dish cans and observed at intervals up to 21 days. The colors of the culture were chosen by comparison with color chips from either the ISCC-NBS Centroid Color Charts or the Dictionary of Color [Maerz, A. and M. R. Paul 2nd. ed. New York: McGraw Hill Book Co., Inc. (1950)].

Yeast Extract-Malt Extract Agar—Growth excellent; vegetative growth grayish yellow brown; aerial mycelium, none to very sparse, white, spore chains and sporangium-like structures present; yellow brown soluble pigment; characteristic crystals present in agar.

Oatmeal Agar—Growth good; vegetative growth off-white to yellow brown; aerial mycelium sparse, white, numerous spore chains and sporangium-like bodies present; no soluble pigment; characteristic crystals present in agar.

Glycerol-Asparagine Agar—Growth fair to good; vegetative growth pale yellow brown; aerial mycelium sparse to moderate, white, a few spore chains but few, if any, sporangium-like structures present; pale grayish yellow brown soluble pigment; characteristic crystals present in agar.

Inorganic-Salts Starch Agar—Growth good; vegetative growth off-white to yellow brown; aerial mycelium sparse, white, spore chains and sporangium-like structures present; no soluble pigment; characteristic crystals present in agar.

Czapek-Sucrose Agar—Growth good; vegetative growth off-white to yellow brown; aerial mycelium sparse, white, spore chains and sporangium-like structures present; pale grayish yellow to pale yellow brown soluble pigment present; characteristic crystals present in agar.

Bennett's Agar—Growth good to excellent; vegetative growth grayish yellow brown; aerial mycelium, none to sparse, white, spore chains and sporangium-like structures present; yellow brown soluble pigment; no crystals detected in agar.

Nutrient Agar—Growth fair to good; vegetative growth yellow brown; aerial mycelium sparse to moderate, white, few spore chains and few sporangium-like structures present; yellow brown soluble pigment; characteristic crystals variably present in agar.

Thin Potato-Carrot Agar—Growth fair, relatively flat; vegetative growth off-white to yellow brown; aerial mycelium sparse to moderate, white, numerous spore chains and sporangium-like structures present; no soluble pigment; no crystals detected in agar.

Peptone-Yeast Extract Iron Agar—Growth good; vegetative growth bronze brown (Maerz & Paul 16C9); aerial mycelium, none; dark brownish black soluble pigment; no crystals detected in agar.

Starch-Casein Nitrate Agar—Growth good; vegetative mycelium off-white to yellow brown; aerial mycelium sparse, white, spore chains and sporangium-like structures present; pale yellow brown soluble pigment variably present; characteristic crystals present in agar.

Yeast Extract-Glucose Agar—Growth good to excellent; vegetative growth dark yellow brown to grayish yellow brown; aerial mycelium, none visible, under 400X sparse spore chains but no sporangium-like structures present; dark yellow brown soluble pigment; characteristic crystals present in agar.

A comparison of the description of *K. aridum* with the descriptions of actinomycetes listed in Bergey's Manual of Determinative Bacteriology, the Approved List of Bacterial Names and other recent taxonomic literature indicates that *K. aridum* differs significantly from previously described species of actinomycetes and cannot be accommodated in any of the previously described genera of the actinomycetes. Sporangia, where present in other actinomycete genera, are true spore vesicles; at maturity they contain aplanospores or zoospores which are eventually released by rupture or dissolution of the sporangial wall. Despite extensive observation and manipulation, the release of spores from the sporangium-like structuress of *K. aridum* was never observed. When placed on agar, the sporangium-like structures of *K. aridum* germinate by the production of one or more germ tubes directly from the sporangium-like structure.

Type culture ATCC 39323 is hereby described as a species of a new genus *Kibdelosporangium aridum*, (from kibdelos, Gr. adj., false, ambiguous; spora Gr. n., a seed; angium Gr. n., a vessel); the specific epithet, *aridum*, (aridus Gr. n., L. adj., dry, arid) refers to the desert soil from which the culture was isolated.

PREPARATION OF THE AAD 216 COMPLEX

The AAD 216 complex may be produced by cultivating a strain of Kibdelosporangium having the characteristics of ATCC 39323 or an active mutant or derivative thereof, obtained by procedures known to the art, under submerged aerobic conditions in an aqueous nutrient medium. The organism is grown in a nutrient medium containing an assimilable carbon source, for example an assimilable carbohydrate. Examples of suitable carbon sources include sucrose, lactose, maltose, mannose, fructose, glucose, and soluble starch. The nutrient medium should also contain an assimilable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the AAD 216 complex can be effected at any temperature conducive to satisfactory growth of the organism, e.g., 15°–42° C., and is conveniently carried out at a temperature of about 25° to 28° C.

The medium normally is neutral, but the exact pH can be varied between 5.0 and 9.0 depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the vegetative cells of the organism. After obtaining an inoculum in this manner, it is transfered aseptically to the fermentation tank medium for large scale production of the antibiotics. The medium used for the vegetative inoculum can be the same as that employed for larger fermentations, although other media can be employed.

As is customary in aerobic submerged culture processes, sterile air is sparged through the culture medium. Agitation may be maintained by means of agitators generally familar to those in the fermentation industry.

In general, optimum production of the complex is achieved after incubation periods of about 144–186 hours in stir-jar fermentors or tank fermentors. The course of the fermentation can be followed by analytical HPLC.

The AAD 216 complex so produced contains the novel bioactive components or individual antibiotic factors, AAD 216A, AAD 216B and AAD 216C which can be isolated as described above.

BIOLOGICAL ACTIVITY DATA

The in vitro minimum inhibitory concentration (MIC) of the AAD 216 complex, enriched AAD 216 complex, AAD 216A, AAD 216B, AAD 216C and vancomycin were determined for a number of microorganisms using the standard microtiter assay procedures. The results are shown in the following Tables A–E.

TABLE A

| | Antimicrobial Spectrum | | | | |
|---|---|---|---|---|---|
| | MIC in µg/ml | | | | |
| Test Organism | AAD 216 Complex | AAD 216 A | AAD 216 B | AAD 216 C | Vancomycin |
| *Staph. aureus* HH127 | 6.3 | 3.1 | 3.1 | 3.1 | 1.6 |
| *Staph. aureus* SK & F 910 | 12.5 | 3.1 | 3.1 | 3.1 | 1.6 |
| *Strep. faecilis* HH34358 | 1.6 | 0.4 | 0.4 | 0.8 | 3.1 |
| *Proteus mirabilis* SK & F 444 | >100 | >100 | >100 | >100 | 100 |
| *E. coli* 12140 (SK & F 809) | >100 | >100 | >100 | >100 | 100 |
| *Kleb. pneumoniae* 4200 (SK & F 798) | >100 | >100 | >100 | >100 | >100 |
| *Pseudomonas aeruginosa* HH63 | >100 | >100 | >100 | >100 | >100 |
| *Serratia marcesens* ATCC 13880 | >100 | >100 | >100 | >100 | >100 |
| *Proteus morgani* SK & F 179 | >100 | >100 | >100 | >100 | >100 |
| *Providencia* SK & F 276 | >100 | >100 | >100 | >100 | >100 |
| *Enterobacter cloacae* HH31254 | >100 | >100 | >100 | >100 | >100 |
| *Salmonella gallinarum* BC595 | >100 | >100 | >100 | >100 | 25 |
| *Staph. epidermidis* SK & F 2479 | 25 | 6.3 | 6.3 | 6.3 | 1.6 |
| *Listeria monocytogenes* SK & F 2255 | 3.1 | 0.8 | 0.4 | ~0.4 | 1.6 |

TABLE A-continued

Antimicrobial Spectrum

| | MIC in μg/ml | | | | |
|---|---|---|---|---|---|
| Test Organism | AAD 216 Complex | AAD 216 A | AAD 216 B | AAD 216 C | Vancomycin |
| *Staph. epidermidis* SK & F 651 | 100 | 50 | 25 | 25 | 1.6 |

TABLE B

(Methicillin Sensitive)

| | MIC in μg/ml | | | | |
|---|---|---|---|---|---|
| Test Organism | AAD 216 Complex | AAD 216 A | AAD 216 B | AAD 216 C | Vancomycin |
| *Staph. aureus* HH127 | 12.5 | 1.6–3.1 | 3.1 | 3.1 | 1.6 |
| *Staph. aureus* SK & F 674 | 12.5 | 3.1–6.3 | 6.3 | 12.5 | 1.6 |
| *Staph. aureus* SK & F 910 | 12.5 | 3.1 | 6.3 | 6.3 | 1.6 |
| *Staph. aureus* SK & F 1761 | 12.5 | 3.1 | 3.1 | 3.1 | 1.6 |
| *Staph. aureus* SK & F 2593 | 25 | 6.3 | 6.3 | 6.3 | 1.6 |
| *Staph. aureus* SK & F 2666 | 12.5 | 3.1 | 3.1 | 6.3 | 1.6 |
| *Staph. aureus* SK & F 2677 | 25 | 6.3 | 3.1 | 6.3 | 1.6 |
| *Staph. aureus* SK & F 2678 | 25 | 6.3 | 6.3 | 6.3 | 1.6 |
| *Staph. aureus* SK & F 2680 | 12.5 | 3.1–6.3 | 6.3 | 6.3 | 1.6 |
| *Staph. aureus* SK & F 2682 | 25 | 3.1–6.3 | 6.3 | 3.1 | 1.6 |
| *Staph. aureus* SK & F 2736 | 25 | 3.1–6.3 | 6.3 | 6.3 | 1.6 |
| *Staph. aureus* SK & F 2776 | 50 | 12.5 | 6.3 | 12.5 | 1.6 |
| *Staph. aureus* SK & F 2777 | 12.5 | 3.1 | 3.1 | 3.1 | 0.8 |
| *Staph. aureus* SK & F 2613 | 6.3 | 1.6 | 1.6 | 1.6 | 1.6 |
| *Staph. aureus* SK & F 2615 | 12.5 | 3.1–6.3 | 6.3 | 6.3 | 3.1 |

TABLE C

(Methicillin Resistant)

| | MIC in μg/ml | | | | |
|---|---|---|---|---|---|
| Test Organism | AAD 216 Complex | AAD 216 A | AAD 216 B | AAD 216 C | Vancomycin |
| *Staph. aureus* SK & F 675 | 50 | 12.5 | 6.3 | 12.5 | 1.6 |
| *Staph. aureus* SK & F 2612 | 12.5 | 6.3 | 3.1 | 6.3 | 1.6 |
| *Staph. aureus* SK & F 2614 | 6.3 | 3.1 | 3.1 | 3.1 | 1.6 |
| *Staph. aureus* SK & F 2616 | 25 | 6.3–12.5 | 6.3 | 6.3 | 0.8 |
| *Staph. aureus* SK & F 2620 | 25 | 6.3 | 12.5 | 12.5 | 3.1 |
| *Staph. aureus* SK & F 2621 | 25 | 6.3 | 6.3 | 6.3 | 1.6 |
| *Staph. aureus* SK & F 2594 | 25 | 6.3–12.5 | 6.3 | 6.3 | 1.6 |
| *Staph. aureus* SK & F 2589 | 25 | 6.3–12.5 | 6.3 | 6.3 | 1.6 |
| *Staph. aureus* SK & F 2590 | 25 | 6.3–12.5 | 3.1 | 6.3 | 1.6 |
| *Staph. aureus* SK & F 2591 | 25 | 6.3 | 6.3 | 6.3 | 1.6 |
| *Staph. aureus* SK & F 2592 | 50 | 6.3 | 12.5 | 12.5 | 3.1 |
| *Staph. aureus* SK & F 2595 | 25 | 6.3–12.5 | 6.3 | 6.3 | ~1.6 |
| *Staph. aureus* SK & F 2596 | 25 | 6.3–12.5 | 6.3 | 6.3 | 3.1 |
| *Staph. aureus* SK & F 2597 | 25 | 6.3–12.5 | 6.3 | 12.5 | 3.1 |

TABLE D

(Anaerobes)

| | MIC in μg/ml | | | | |
|---|---|---|---|---|---|
| Test Organism | AAD 216 Complex | AAD 216 A | AAD 216 B | AAD 216 C | Vancomycin |
| *Bacteroides fragilis* ATCC 25285 | >32 | 32 | 32 | 32 | 32 |
| *B. fragilis* H145 | >32 | 16 | 16 | 8 | 32 |
| *B. fragilis* SK & F 3060 | >32 | 32 | 16 | 16 | 32 |
| *B. loeochii* SK & F 3087 | >32 | 8–16 | 16 | 4 | 32 |
| *B. thetaiotamicron* SK & F 3089 | >32 | >32 | 32 | 32 | 32 |
| *Fusobacterium nucleatum* ATCC 25586 | >32 | 32 | 32 | 32 | 32 |
| *Clostridium perfringens* MCP-1 | ≦0.016 | ≦0.016 | 0.125 | ≦0.016 | 0.5 |
| *C. perfringens* MCP-2 | ≦0.016 | ≦0.016 | 0.125 | ≦0.016 | 0.5 |
| *C. perfringens* ATCC 19408 | 0.25 | 0.031–0.063 | 0.125 | 0.125 | 1.0 |
| *Clostridium difficile* SK & F 3062 | 1.0 | 0.25 | 0.25 | 0.5 | 2 |

TABLE D-continued (Anaerobes)

| | MIC in μg/ml | | | | |
|---|---|---|---|---|---|
| Test Organism | AAD 216 Complex | AAD 216 A | AAD 216 B | AAD 216 C | Vancomycin |
| C. difficile SK & F 3065 | 1.0 | 0.5 | 0.25 | 0.5 | 4 |
| C. difficile SK & F 3091 | ≦0.016 | 0.125–0.25 | 0.25 | 0.031 | 2 |
| C. difficile SK & F 3092 | 1.0 | 0.125 | 0.25 | 0.25 | 2 |
| C. difficile SK & F 3096 | 1.0 | 0.25 | 2 | 0.25 | 2 |
| C. difficile SK & F 3098 | ≦0.016 | ≦0.016 | 2 | 0.031 | 2 |

TABLE E

| | MIC in μg/ml | | |
|---|---|---|---|
| Test Organism | Enriched AAD 216 Complex | AAD 216A | Vancomycin |
| Staph. aureus HH 127 | 6.3 | 6.3 | 3.1 |
| Staph. aureus SK & F 910 | ~6.3 | 6.3 | 3.1 |
| Staph. aureus 209P | 1.6 | 1.6 | 1.6 |
| Staph. aureus 209P-Mutant | 100 | 100 | >100 |
| Staph. aureus SK & F 674 | 6.3 | 3.1 | 1.6 |
| Staph. aureus SK & F 674-P6 Mutant | ~100 | ~100 | >100 |
| Staph. aureus SK & F 675 | 12.5 | 12.5 | 3.1 |
| Staph. epidermidis SK & F 2479 | 25 | 25 | 6.3 |
| Staph. epidermidis SK & F 2683 | 100 | 100 | 6.3 |
| Staph. epidermidis SK & F 651 | 100 | 100 | 6.3 |
| Staph. epidermidis SK & F 2265 | 100 | 100 | 6.3 |
| Strep. faecalis HH 34358 | 0.4 | 1.6 | 6.3 |
| Strep. faecalis SK & F 657 | 0.4 | 0.8 | 3.1 |
| Listeria monocytogenes SK & F 2255 | 0.8 | 1.6 | 3.1 |
| E. coli 12140 (SK & F 809) | >100 | >100 | >100 |
| Salmonella gallinarum BC595 | >100 | >100 | >100 |

The in vivo activity of the AAD 216A, AAD 216B, AAD 216C and vancomycin, measured as $ED_{50}$, was demonstrated against intraperitoneal s.c. infections with 46.8 $LD_{50}$'s of Staph. aureus HH 127 in mice by treatments with the antibiotics 1 and 5 hours post infections. The $ED_{50}$'s were as follows: AAD 216A, 5.0 mg/kg; AAD 216B, 5.0 mg/kg; AAD 216C, 7.5 mg./kg; vancomycin, 1.76 mg/kg.

The antibiotic compounds of the present invention including AAD 216 complex and its major bioactive components; AAD 216A, AAD 216B and AAD 216C and mixtures thereof, exhibit antibacterial activity. The invention includes within its scope pharmaceutical compositions containing at least one of the above-mentioned antibiotic compounds and a pharmaceutically acceptable carrier. The compositions may also contain other active antibacterial agents. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixers; and preparations for parenteral administration such as sterile solutions, suspensions or emulsions.

For use as an antibacterial agent, the compositions are administered so that the concentration of the active ingredient is greater than the minimum inhibitory concentration for the particular organism treated.

The activity of the AAD 216 complex, and its components; AAD 216A, AAD 216B and AAD 216C was demonstrated in vitro against a total of 58 bovine mastitis isolates using the conventional agar dilution method to determine minimum inhibitory concentrations (MICs). The MICs for the AAD 216 complex, AAD 216A, AAD 216B and AAD 216C ranged from 0.25 to >128 μg/ml., 0.13 to >128 μg/ml, 0.06 to >128 μg/ml and 0.06 to >128 μg/ml respectively. In comparison, vancomycin has MICs for the same microorganisms ranging from 0.25 to >128 μg/ml.

GROWTH PROMOTANT ACTIVITY

The growth promotant activities of the AAD 216 complex, and its components; AAD 216A, AAD 216B and AAD 216C were determined in a swine in vitro model to predict utility in monogastric animals, such as swine and poultry; a rumen in vitro model to predict utility in beef, dairy and sheep production and in vivo in a chick growth model.

Swine in vitro model

A Yorksire barrow is surgically prepared either with an ileal cannula, which is placed 15 cm. from the ileocecocolic junction, or a cecal cannula, which placed midway between the apex and origin of the cecum. The animal is fed 4 times daily to restrict intake to 4.5% of body weight in a 30 kg animal or 2.5% of body weight in a 100 kg animal. The swine grower ration is:

| | (% w/w) | (lbs/ton) |
|---|---|---|
| Medium ground shelled corn | 70.60 | 1412 |
| Soybean meal, 44% | 22.00 | 440 |
| Dehydrated alfalfa meal, 17% | 4.50 | 90 |
| Calcium propionate | 0.15 | 3 |
| Vitamin/mineral premix | 2.75 | 55 |

Sampling of the material, via the cannula, begins 150–180 minutes following the first morning feeding and continues any time from 30–120 minutes thereafter, depending on the quantity of material needed. The sample is maintained in crushed ice, no cooler than 5° C., and is gassed continuously with carbon dioxide. The collected material is filtered. The filtrate is the inoculum used for incubations of the test and control samples. The gassed inoculum, 2.25 ml, is placed in each of 10 gassed test tubes, each containing 0.75 ml of a nutrient solution and 0.5 mg of each test compound. Four blank control tubes, along with the test compound tubes, are incubated 5 hours at 37° C. with agitation. Four more killed tubes are included which are not incubated.

The tubes are each treated with 0.60 ml of a 25% solution of metaphosphoric acid, then, stored at −4° C. until analysis. Samples are thawed and centrifuged for 25 minutes at 20,000 r.p.m. The supernatant liquid is decanted, sampled for gas chromatography and automatic analysis. The results are fed into a computer for finishing to give figures in which the blank control value is 100%. Virginiamycin and vancomycin are used as positive controls.

| Compound (ppm) | VFA* (% Control) | LYS* (% Control) | GLU* (% Control) | LAC* (% Control) |
|---|---|---|---|---|
| Virginiamycin | | | | |
| (166.67) | 93 | 163 | 197 | 81 |
| (16.67) | 130 | 127 | 191 | 76 |
| (1.67) | 248 | 82 | 182 | 70 |
| Vancomycin | | | | |
| (166.67) | 250 | 48 | 190 | 64 |
| (16.67) | 280 | 42 | 189 | 59 |
| (1.67) | 92 | 83 | 100 | 99 |
| AAD 216 Complex | | | | |
| (666.67)** | 267 | 44 | 189 | 58 |
| (166.67) | 345 | 50 | 195 | 51 |
| (66.67) | 390 | 53 | 188 | 46 |
| (16.67) | 124 | 81 | 113 | 93 |
| (6.67) | 90 | 101 | 96 | 100 |
| AAD 216A | | | | |
| (166.67) | 326 | 63 | 187 | 58 |
| (16.67) | 379 | 50 | 191 | 47 |
| (1.67) | 101 | 94 | 97 | 99 |
| AAD 216B | | | | |
| (166.67) | 290 | 50 | 190 | 56 |
| (16.67) | 365 | 55 | 184 | 47 |
| (1.67) | 102 | 98 | 97 | 98 |
| AAD 216C | | | | |
| (166.67) | 294 | 42 | 191 | 57 |
| (16.67) | 398 | 53 | 188 | 45 |
| (1.67) | 101 | 95 | 96 | 98 |

*VFA refers to the total of volatile fatty acids, namely acetate, propionate, isobutyrate, butyrate, isovalerate and valerate. LYS is lysine, GLU is glucose and LAC is L-lactic acid.
**AAD 216 complex contains 25% of a mixture of AAD 216A, AAD 216B and AAD 216C.

RUMEN IN VITRO MODEL

The protocol for the rumen in vitro model is analogous to the protocol for the swine in vitro model with the following modifications:

(1) A 400 kg steer is surgically prepared with a rumen cannula.

(2) The animal is fed one time a day with the following ration:

| | % w/w |
|---|---|
| Finished Feed | |
| Cottonseed hulls | 44.0 |
| Cracked corn | 22.0 |
| Alfalfa Hay 1" | 20.0 |
| Pellet Supplement* | 10.0 |
| Liquid Molasses | 4.0 |
| | 100.0 |
| *Pellet Supplement | |
| Soybean Oil Meal (50% protein) | 50.0 |
| Medium Ground Corn | 32.5 |
| D/Calcium Phosphate | 6.50 |
| Plain salt | 2.50 |
| Ground limestone (Thomasville) | 3.50 |
| Urea | 2.50 |
| Vitamin A & D$_2$ Premix** | 2.50 |
| | 100.00 |
| **Vitamin A & D$_2$ Premix | |
| Vitamin A (30,000 IU/gm) | 5.87 |
| Vitamin D$_2$ (16,000,000 IU/lb) | 0.50 |
| Fine ground corn | 93.63 |
| | 100.00 |

(3) Manipulation of VFA production is described as the production ratio of propionate as a percentage of total VFA produced.

(4) Sampling of the material, via the cannula, is at 120 minutes post feeding.

| Compound (ppm) | VFA* (% Control) | LYS* (% Control) | GLU* (% Control) | Propionate % (% Control) |
|---|---|---|---|---|
| Vancomycin | | | | |
| (50.0) | 107 | 97 | 189 | 127 |
| (5.0) | 108 | 85 | 165 | 130 |
| (0.5) | 97 | 83 | 17 | 105 |
| Avoparcin | | | | |
| (50.0) | 113 | 97 | 141 | 132 |
| (5.0) | 105 | 85 | 166 | 121 |
| (0.5) | 103 | 96 | 116 | 106 |
| Monensin Sodium | | | | |
| (50.0) | 109 | 147 | 0 | 156 |
| (5.0) | 104 | 141 | 126 | 149 |
| (0.5) | 94 | 109 | 11 | 119 |
| AAD 216 Complex | | | | |
| (200.0)** | 118 | 116 | 78 | 159 |
| (50.0)** | 117 | 101 | 11 | 159 |
| (20.0)** | 115 | 95 | 193 | 130 |
| (2.0)** | 101 | 92 | 60 | 102 |
| AAD 216A | | | | |
| (50.0) | 111 | 114 | 153 | 146 |
| (5.0) | 93 | 90 | 28 | 135 |
| (0.5) | 94 | 96 | 121 | 105 |
| AAD 216B | | | | |
| (50.0) | 111 | 124 | 20 | 148 |
| (5.0) | 121 | 107 | 0 | 141 |
| (0.5) | 100 | 103 | 45 | 103 |
| AAD 216C | | | | |
| (50.0) | 101 | 110 | 0 | 151 |
| (5.0) | 111 | 96 | 45 | 136 |
| (0.5) | 83 | 103 | 29 | 120 |

*VFA refers to the total of volatile fatty acids, namely acetate, propionate, isobutyrate, butyrate, isovalerate and valerate. LYS is lysine, and GLU is glucose.
**AAD 216 complex contains 25% of a mixture of AAD 216A, AAD 216B and AAD 216C.

CHICK GROWTH STUDY

One day old broiler chicks, selected for weight, health and sex, are housed in an environmentally controlled room with temperature at 80° F. and humidity at 40%. Chicks are fed ad libitum. Water is offered ad libitum. A rye or corn basal ration is fed during the acclimation period (days 1 and 2), then, mixed with the compound under test or control conditions on days 3-17. Either 8 pens (64 chicks) or 16 pens (128 chicks) are used for each test or control group.

| Diet Ingredients | Basal Rye Diet (% w/w) | (lbs/ton) |
|---|---|---|
| Ground Rye (fine grind) | 54.4 | 1088 |
| Soybean Meal (49% protein) | 27 | 540 |
| Meat & Bone meal (50% protein) | 10 | 200 |
| Dehydrated Alfalfa meal | 1.25 | 25 |
| Fat, animal | 4 | 80 |
| Dried Whey (or lactose) | 1 | 20 |
| Ground Limestone | 0.67 | 13.4 |
| Dicalcium Phosphate | 0.50 | 10 |
| Iodized salt | 0.23 | 4.6 |
| Vitamin premix | 0.175 | * |
| Trace mineral premix | 0.25 | 5 |
| DL methionine (98%) | 0.45 | 9 |
| Choline Chloride (50% aqueous sol.) | 0.150** | 3 |

*Vitamin premix will be mixed into diets when test chemicals are added. 87.5 g vitamin premix/49,912.5 g of basal rye diet.
**Since choline is added as a 50% aqueous solution, percentages in diet is doubled.

| | Dose PPM | # of Reps | Weight Day 10 | Weight Day 17 | Feed/Gain 3-10 | Feed/Gain 10-17 | Feed/Gain 3-17 | # of D. Cks |
|---|---|---|---|---|---|---|---|---|
| | | | | | % of Control | | | |
| Virginiamycin | 10.0 | 8 | 103.8 | 116.0 | 97.4 | 83.6 | 90.4 | 2 |
| Virginiamycin | 50.0 | 8 | 105.0 | 121.3 | 93.2 | 74.6 | 83.2 | 1 |
| AAD 216 Complex* | 40.0 | 8 | 107.7 | 132.4 | 90.9 | 69.6 | 79.6 | 2 |
| AAD 216 Complex* | 160.0 | 8 | 106.1 | 117.1 | 91.0 | 80.1 | 85.3 | 3 |
| | | | GRAMS | | GRAMS/GRAM | | | |
| Control | 0.0 | 8 | 164.2 | 280.4 | 1.577 | 2.815 | 2.209 | 2 |
| Rye Historic Control | | | 169.1 | 298.4 | 1.566 | 2.563 | 2.080 | |
| C.V. Among Pens - 3.71% | | | | | | | | |

*AAD 216 complex contains 25% of a mixture of AAD 216A, AAD 216B and AAD 216C.

The feed compositions of this invention comprise the normal feed rations of the meat and milk producing animals supplemented by a quantity of an active ingredient selected from the group consisting of AAD 216 complex, AAD 216A, AAD 216B, AAD 216C or a mixture thereof which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are as follows:

A swine ration for growing hogs of 40-100 pounds body weight is prepared using the following formula:

| Corn, ground | 78.15% |
|---|---|
| Soybean oil meal, 44% | 17.0% |
| Meat scraps, 50% | 3.0% |
| Oyster shell flavor | 0.4% |
| Bone meal | 0.5% |
| Zinc oxide | 0.01% |
| Vitamin A, B, B$_{12}$ & D supplement | optional |

A chicken ration for broilers is prepared using the following formula:

| Yellow corn meal | 67.35% |
|---|---|
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin B$_{12}$ | 0.10% |
| Manganese sulfate | 0.02% |
| Vitamin mix | 0.06% |

Swine feed from weanling to fattening or finishing rations may be supplemented. Swine eat from about 2 lb. of ration per day (for a 25 lb. pig) to 9 lg. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations, often, contain high energy supplements such as added fats, proteins and vitamins. Turkey rations are similar, but comprise only a starting ration and a growing ration. Chickens or pheasants eat from 0.03-0.3 lbs. of feed per day, turkeys twice that much. Estimated intake of feed is dependent on the weight and age of the meat producing animal.

The active ingredients selected from the group consisting of AAD 216 complex, AAD 216A, AAD 216B, AAD 216C or a mixture thereof are mixed uniformly with such feed rations to give supplemented rations which are, then fed as to custom, which is, most often, ad libitum. Conveniently, to do this, a premix of the supplemental growth promotant of this invention, optionally combined with or without other supplements known to this art such as an anthelmintic, a nitrogen source or an antibiotic, for example, virginiamycin or oxytetracycline is prepared by the manufacturer for sale to the formulators or feed lot operators. The concentration of the active ingredients selected from the group consisting of AAD 216 complex, AAD 216A, AAD 216B, ADD 216C or a mixture thereof in the premix is usually from 5-75% by weight or a concentration 100-2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the active ingredients selected from the group consisting of AAD 216 complex, AAD 216A, AAD 216B, AAD 216C or a mixture thereof in the complete ration is a nontoxic but active quantity chosen, for example, from a range of about 1-1000 parts of active ingredient by weight per million parts of whole feed (ppm) or about 2-115 grams per ton. Advantageously, a nontoxic quantity of active ingredient is chosen from the range of 10-50 ppm.

The method of this invention comprises feeding to monogastric or ruminant, meat or milk producing animals, especially beef and dairy cattle, sheep, swine and poultry, an effective growth promoting but nontoxic quantity of an active ingredient selected from the group consisting of AAD 216 complex, AAD 216A, AAD 216B, AAD 216C or a mixture thereof. Other monogastric animals whose digestive tract also features fermentation in a cecum or cecum-like chamber are rabbits and horses.

The supplemented feed rations, described above, are presented to the animal by methods known to the art. Ad libitum feeding in the pasture, pen or growing shed is most convenient to increase the growth and milking rate of the animal and to increase the feed efficiency of the operation.

The following examples are illustrative of the product, isolation and purification of the antibiotics of the present invention and are not therefore to be considered in limiting the present invention as described in the claims appended hereto.

The nutrient media employed in the following examples have the compositions listed below. The yields for the fermentations were obtained by analytical HPLC by comparison to quantitated authentic samples.

Medium 13 (H) was used for the seed growth of SK&F-AAD 216 throughout the experiments. Ingredients of medium 13H are: starch, 15 g/l; sucrose, 5 g/l; dextrose, 5 g/l; HY-soy, 7.5 g/l; corn steep liquor, 5 g/l; $K_2HPO_4$, 1.5 g/l; NaCl, 0.5 g/l; $CaCO_3$, 1.5 g/l; and Mineral "S", 5 ml/l; pH to 7.0.

Mineral "S" has the following compositions: $ZnSO_4 7H_2O$, 2.8 g/l; $Fe(NH_4)_2HC_6H_5O_7$, 2.7 g/l; $CuSO_4.5H_2O$, 0.125 g/l; $MnSO_4.H_2O$, 1.0 g/l; $CoCl_2.6H_2O$, 0.1 g/l; $Na_2B_4O_7.H_2O$, 0.09 g/l; and $Na_2MoO_4.2H_2O$, 0.05 g/l.

The ingredients of medium V-2 are: soybean flour, 15 g/l; beet molasses, 10 g/l; glucose, 10 g/l; Estrasan 4 (methyl oleate), 10 g/l; and NaCl, 0.3 g/l to a pH of 7.2.

EXAMPLE 1

First Seed Stage

The entire growth of a slant of *K. aridum* was suspended in 10 ml of sterile water and aseptically innoculated into a 4 l. aspirator bottle containing 500 ml of medium 13H. After incubation on a rotatory shaker, 250 rpm, at 28° C. for 3 days, the mature culture was then employed to innoculate the 14 l. glass vessel fermentor of Example 2 to produce a second seed stage.

EXAMPLE 2

Second Seed Stage

A 14 l. glass vessel fermentor (New Brunswick Model 19) with 10 l of sterile medium 13H was aseptically inoculated with 500 ml of vegetative culture from Example 1. The vessel was operated according to the following schedule:

Agitation: 400 rpm from 0-72 hr.
Aeration: 0.4 v/v/m* from 0-72 hr.
Temp.: 28° C.

*v/v/m—vol. of air per vol. of medium per minute

Five liters of the resultant vegetative culture was them employed to inoculate the 75 l. fermentor of Example 3 to produce a third seed stage.

EXAMPLE 3

Third Seed Stage

A 75 l. fermentator (Chemapec) was run in similar fashion to Example 2. Fiver liters of the vegetative culture from Example 2 was used to inoculate the 75 l. fermentor containing 50 l. of medium 13H. The fermentation apparatus was operated as follows:

Agitation: 250 rpm from 0-72 hr.
Aeration: 0.4 v/v/m from 0-72 hr.
Temp.: 28° C.

Fifty liters of the resultant vegetative culture was then employed to inoculate the 750 l. fermentor of Example 4 to produce the desired AAD 216 complex.

EXAMPLE 4

Production of AAD 216 Complex

A 750 l. fermentor (ABEC) was operated in a similar fashion to Example 3. Fifty liters of the vegetative culture of Example 3 was used to aseptically inoculate the 750 l. fermentor containing 600 l. of medium V-2. The fermentor was operated as follows:

Agitation: 120 rpm from 0-168 hr.
Aeration: 0.3 v/v/m from 0-168 hr.
Temp.: 26° C.

The fermentation broth contained the AAD 216 complex which was composed of the individual factor antibiotics as follows:

AAD 216A = 50 µg/ml;
AAD 216B = 60.8 µg/ml; and
AAD 216C = 43.5 µg/ml.

EXAMPLE 5

Production of AAD 216 Complex

A 450 l. fermentor (Chemapec) was operated in a similar fashion to Example 4. Thirty liters of vegetative culture (third seed stage) produced according to Example 3 was used to aseptically inoculate the 450 l. fermentor containing 300 l. of medium V-2. The fermentor was operated as follows:

Agitation: 120 rpm from 0-168 hr.
Aeration: 0.4-0.5 v/v/m
Temperature: 26° C.

The fermentation broth contained the AAD 216 complex which was composed of the individual factor antibiotics as follows:

AAD 216A = 46.2 µg/ml
AAD 216B = 75 µg/ml
AAD 216C = 48 µg/ml.

EXAMPLE 6

Isolation of AAD 216 Complex

Whole fermentation broth (600 l.) from Example 4 was clarified by rotary drum filtration (Komline-Sanderson, Laboratory Scale Model) using filter aid (Hyflo Supercel, Johns-Manville Products Corp.) at existing broth pH (pH 7.7-8.2). The broth filtrate (420 l.) was chilled to 4° C. by batch treatment of 100 L. volumes in a vat placed in a cold bath (methanol/dry ice). The chilled broth filtrate was then precipitated by slow addition of concentrated hydrochloric acid, with mixing, to pH 3.0. The resulting precipitate was recovered by rotary vacuum filtration using filter aid as previously described. The filter aid-product precipitate cake was extracted by mixing with deionized water (55 l.) and adjusting to pH 7.0 for 10 minutes. The aqueous extract thus obtained was filtered through Whatman #4 filter paper to remove the filter aid. The filtrate so obtained was applied to two XAD-7 resin columns (8.5×110 cm.) at a flow rate of 0.5 vols./hr. After washing with 8 volumes of deionized water (pH 7.0) the desired AAD 216 complex was recovered by elution with aqueous methanol (50-100%). The methanolic eluate(s) containing the desired AAD 216 complex was concentrated by evaporation using a rising film evaporator at 35° C. The resulting aqueous concentrate was freeze-dried on a Virtis shelf lyophilizer, yielding 85.1 g of AAD 216 complex.

This AAD 216 complex was chromatographed on Whatman Partisil ® Prep 40 ODS-3 (1 kg) in a John Yvon Chromatospac-Prep 100 (step gradient 15 to 33 percent acetonitrile-0.1 M pH 3.2 phosphate buffer) to yield an enriched AAD 216 complex which by analytical HPLC contained 1.88 g. of AAD 216A, 2.6 g. of AAD 216B and 2.8 g of AAD 216C.

EXAMPLE 7

Isolation of AAD 216A, AAD 216B and AAD 216C

A sample of the enriched AAD 216 complex isolated according to Example 6 (38 g. non-desalted) which by analytical HPLC contained 0.42 g. of AAD 216A, 1.39 g. of AAD 216B and 0.08 g. of AAD 216C, was dissolved in one liter 15% acetonitrile in 0.1M pH 6 phosphate buffer and the pH adjusted to 6.3. This solution was loaded onto a Waters Prep 500 ® HPLC with a column of Whatman Partisil ® 40 (ODS-3) (50 cm.×4.8 cm) at a flow rate of 200 ml/minute. The column was then eluted using the following gradient:

(1) 20% aqueous acetonitrile and buffer solution until polar material (ultraviolet detector at 210 nm) was eluted;

(2) 24% acetonitrile buffer solution until AAD 216A was eluted;

(3) 26% acetonitrile buffer solution until AAD 216B was eluted;

(4) 28% acetonitrile buffer solution until AAD 216C was eluted; and (5) 50% aqueous acetonitrile.

The appropriate fractions which were eluted from the HPLC column were then desalted as described below to afford the pure individual antibiotics: AAD 216A, 0.25 g; AAD 216B, 1.05 g; and AAD 216C, 0.06 g.

The desalting procedure involved a pooling of the appropriate fractions from the HPLC and removal of the acetonitrile at reduced pressure. The resulting aqueous samples were loaded onto an XAD-7 resin column and eluted with deionized water until the conductivity of the outflow was less than 25 micro MHO. The column was then eluted with aqueous acetonitrile (40-60%) and the eluant lyophilized to afford the desired products.

EXAPLE 8

Isolation of enriched AAD 216 Complex

A 10 gram sample of AAD 216 complex isolated according to the XAD-7 protocol of Example 6 which contained 0.69 g AAD 216A, 0.23 g AAD 216B and 0.21 g. AAD 216C (HPLC analysis) was dissolved 17.5 percent acetonitrile and 0.1M pH 6 phosphate buffer solution. The pH of the solution was adjusted to 6.3 and this solution was loaded onto a Waters Prep 500 ® high pressure liquid chromatograph equipped with a 50 cm×4.8 cm column packed with Whatman Partisil ® Prep 40 (ODS-3). The column was eluted with 20 percent acetonitrile and buffer solution to remove polar material and then eluted with 28% acetonitrile buffer solution to obtain the enriched AAD 216 complex in the acetonitrile-buffer solution. The acetonitrile in the eluant was removed at reduced pressure and the resulting aqueous solution was loaded onto an XAD-7 resin column and washed with deionized water until the conductivity of the outflow was less than 25 micro HMO. The column was then eluted with aqueous acetonitrile (40-60%) and the eluant lyophilized to afford 2.05 g. enriched AAD 216 complex which contained 0.59 g AAD 216A, 0.20 g AAD 216B and 0.20 g AAD 216C.

EXAMPLE 9

Alternate Isolation Procedure

Alternately, the AAD 216 complex after XAD-7 purification was chromatographed utilizing the procedure in Example 7 to maximize recovery affording AAD 216A, AAD 216B and AAD 216C in relatively pure state.

The AAD 216A so obtained from four individual runs (containing 3.9 g., 2.6 g and 2.2 g of AAD 216A by analytical HPLC) was combined and rechromatographed on the same HPLC isocratically eluting with 22% acetonitrile and 0.1M pH 6 phosphate buffer to afford, after desalting, 4.6 g of AAD 216A from a middle cut in a highly purified state. The other fractions were recycled for further purification.

The AAD 216B so obtained from the same individual runs (containing 2.5 g, 3.7 g, 3.7 g and 1.4 g by analytical HPLC) was combined and rechromatographed on the same HPLC isocratically eluting with 26% acetonitrile and 0.1M pH 6 phosphate buffer to afford, after desalting 2.7 g of AAD 216B from a middle cut in a highly purified state. The other fractions were recycled for further purification.

EXAMPLE 10

Alternate Isolation of Enriched AAD 216 Complex

AAD 216 complex isolated according to the protocol of Example 6 which contained approximately 720 mg of AAD 216A, AAD 216B and AAD 216C was dissolved in water (200 ml) and filtered. The filtrate was mixed with 70 ml of an affinity chromatography sorbent of Affi-Gel ® 10-D ala-D ala (633 mg D ala-D ala) in 0.02M pH 7.0 sodium phosphate buffer [see Cuatrecasas et al., Biochemistry, Vol. 11, No. 12, pp 2291-2298 (1972) for general procedure] and gently stirred for ½ hour. The mixture was poured into a column and the aqueous phase eluted off. The column was washed with: 0.02M pH 7.0 phosphate buffer (2×250 ml); 0.5M NH₄OAc pH 7.8 (2×250 ml.); H₂O (250 ml); 0.1M pH 7.8 NH₄OAc (250 ml); H₂O (250 ml.); 40% aqueous acetonitrile (70 ml.); 40% aqueous acetonitrile (1400 ml); and 30% acetonitrile in 0.4M NaHCO₃ (2×250 ml). The 1400 ml—40% aqueous acetonitrile fraction was lyophilized to yield 607 mg of the enriched AAD 216 complex containing 224 mg AAD 216A, 133 mg AAD 216B and 158 mg AAD 216C.

What is claimed is:

1. A biologically pure culture of the microorganism *Kibdelosporangium aridum* Shearer gen. nov., sp. nov. ATCC 39323 or an active mutant thereof, said microorganism and mutant being capable of producing AAD 216A, AAD 216B or AAD 216C in recoverable quantity upon cultivation in aqueous nutrient medium containing assimilable sources of nitrogen and carbon.

2. A culture of the microorganism according to claim 1, which is capable of producing an antibiotic complex containing a mixture of AAD 216A, AAD 216B and AAD 216C.

* * * * *